(12) United States Patent
Yu (10) Patent No.: US 9,937,226 B2
(45) Date of Patent: Apr. 10, 2018

(54) USE OF IMMUNOMODULATORY PROTEIN FROM GANODERMA IN INHIBITING CANCER STEM CELLS

(71) Applicant: MYCOMAGIC BIOTECHNOLOGY CO., LTD, New Taipei (TW)

(72) Inventor: Cheng-Chia Yu, Taichung (TW)

(73) Assignee: MYCOMAGIC BIOTECHNOLOGY CO., LTD., New Taipei (TW)

( * ) Notice: Subject to any disclaimer, the term of this patent is extended or adjusted under 35 U.S.C. 154(b) by 0 days.

(21) Appl. No.: 14/982,519

(22) Filed: Dec. 29, 2015

(65) Prior Publication Data

US 2016/0184389 A1 Jun. 30, 2016

Related U.S. Application Data

(60) Provisional application No. 62/097,420, filed on Dec. 29, 2014.

(51) Int. Cl.
*A61K 38/16* (2006.01)
*C07K 14/37* (2006.01)
*C07K 14/375* (2006.01)
*A61K 45/06* (2006.01)

(52) U.S. Cl.
CPC ............ *A61K 38/16* (2013.01); *A61K 45/06* (2013.01); *C07K 14/375* (2013.01)

(58) Field of Classification Search
None
See application file for complete search history.

(56) References Cited

U.S. PATENT DOCUMENTS

| 7,601,808 | B2 * | 10/2009 | Lin | C07K 14/375 |
| | | | | 530/350 |
| 8,476,238 | B2 * | 7/2013 | Ko | A61K 31/517 |
| | | | | 424/649 |
| 8,846,633 | B2 * | 9/2014 | Chiou | A61K 31/7088 |
| | | | | 514/44 A |
| 9,018,171 | B2 * | 4/2015 | Ko | A61K 31/282 |
| | | | | 424/649 |
| 9,161,964 | B2 * | 10/2015 | Ko | A61K 38/168 |
| 9,827,288 | B2 * | 11/2017 | Hsu | A61K 38/16 |
| 2007/0207954 | A1 * | 9/2007 | Lin | C07K 14/375 |
| | | | | 530/350 |
| 2011/0318429 | A1 * | 12/2011 | Ko | A61K 31/517 |
| | | | | 424/649 |
| 2013/0296253 | A1 * | 11/2013 | Ko | A61K 38/168 |
| | | | | 514/19.8 |
| 2014/0045841 | A1 * | 2/2014 | Huang | A61K 45/06 |
| | | | | 514/234.5 |
| 2014/0086946 | A1 * | 3/2014 | Ko | A61K 31/282 |
| | | | | 424/185.1 |
| 2016/0115208 | A1 * | 4/2016 | Chao | A61K 38/168 |
| | | | | 514/17.8 |
| 2016/0184389 | A1 * | 6/2016 | Yu | A61K 38/16 |
| | | | | 424/185.1 |
| 2017/0173110 | A1 * | 6/2017 | Ko | A61K 38/168 |

FOREIGN PATENT DOCUMENTS

| CN | 102199201 A1 * | 9/2011 |
| TW | 1299735 B * | 8/2008 |
| WO | WO 2015/135483 A1 * | 9/2015 |
| WO | WO 2016/034081 A1 * | 3/2016 |
| WO | WO 2016/062239 A1 * | 4/2016 |

OTHER PUBLICATIONS

Lin et al, Process Biochemistry, 2010, 45:1537-1542.*
Chiu et al, PLoS ONE, May 6, 2015, 10/5:e0125774, doi:10.1371/journal,pone.0125774, 23 pages.*
Hsin et al, Autophagy, Aug. 2011, 7:8, 873-882.*
Hsin et al, Mol. Pharmaceutics, Mar. 26, 2015, 12:1534-1543.*
Li et al, Critical Reviews in Biotechnology, Jun. 9, 2011, 31/4:365-375.*
Lin et al, J. Agric. Food Chem., 2010, 58/22:12014-12021.*
Mahajna et al, Nutrition and Cancer, 2009, 61/1:16-26.*
Wang et al, Current Topics in Nutraceutical Research, 2012, 10/1:1-12.*
Wasser, Appl. Microbiol. Biotechnol., 2011, 89:1323-1332.*
Xu et al, J. Agricultural and Food Chemistry, Mar. 20, 2016, 64:2690-2698.*
Zaidman et al, Appl. Microbiol., Biotechnol., 2005, 67:453-468.*
Danaraddi et al, Journal of Oral Research and Review, Jan.-Jun. 2014, 6/1:34-39.*
Kao et al, Functional Foods in Health and Disease, 2013, 3/2:48-65, publication date—Feb. 9, 2013.*
Wang et al, Oncotarget, www.impactjournals.com/oncotarget, 9 pages. Published: Jul. 21, 2017.*
El Enshasy et al, Trends in Biotechnology, Dec. 2013, 31/12:668-677.*
Choi et al, Journal Dental Research, 2008, 81/1:14-32.*

* cited by examiner

*Primary Examiner* — Nita M Minnifield
(74) *Attorney, Agent, or Firm* — WPAT, P.C., Intellectual Property Attorneys; Anthony King (57) ABSTRACT

The present invention relates to a new use of an immunomodulatory protein derived from *Ganoderma* or a recombinant or a composition thereof in inhibiting cancel stem cells. Particularly, the immunomodulatory protein is derived form *Ganoderma microsporum* and the cancel stem cell is oral cancer stem cell.

2 Claims, 7 Drawing Sheets

SEQUENCE LISTING

<160> NUMBER OF SEQ ID NOS: 4

<210> SEQ ID NO 1
<211> LENGTH: 6
<212> TYPE: PRT
<213> ORGANISM: Ganoderma microsporum

<400> SEQUENCE: 1

Leu Ala Trp Asn Val Lys
1               5

<210> SEQ ID NO 2
<211> LENGTH: 10
<212> TYPE: PRT
<213> ORGANISM: Ganoderma microsporum

<400> SEQUENCE: 2

Asp Leu Gly Val Arg Pro Ser Tyr Ala Val
1               5                   10

<210> SEQ ID NO 3
<211> LENGTH: 111
<212> TYPE: PRT
<213> ORGANISM: Ganoderma microsporum

<400> SEQUENCE: 3

Met Ser Asp Thr Ala Leu Ile Phe Thr Leu Ala Trp Asn Val Lys Gln
1               5                   10                  15

Leu Ala Phe Asp Tyr Thr Pro Asn Trp Gly Arg Gly Arg Pro Ser Ser
            20                  25                  30

Phe Ile Asp Thr Val Thr Phe Pro Thr Val Leu Thr Asp Lys Ala Tyr
        35                  40                  45

Thr Tyr Arg Val Val Val Ser Gly Lys Asp Leu Gly Val Arg Pro Ser
    50                  55                  60

Tyr Ala Val Glu Ser Asp Gly Ser Gln Lys Ile Asn Phe Leu Glu Tyr
65                  70                  75                  80

Asn Ser Gly Tyr Gly Ile Ala Asp Thr Asn Thr Ile Gln Val Tyr Val
                85                  90                  95

Ile Asp Pro Asp Thr Gly Asn Asn Phe Ile Val Ala Gln Trp Asn
            100                 105                 110

<210> SEQ ID NO 4
<211> LENGTH: 140
<212> TYPE: PRT
<213> ORGANISM: Ganoderma microsporum

<400> SEQUENCE: 4

Glu Ala Glu Ala Glu Phe Met Ser Asp Thr Ala Leu Ile Phe Thr Leu
1               5                   10                  15

Ala Trp Asn Val Lys Gln Leu Ala Phe Asp Tyr Thr Pro Asn Trp Gly
            20                  25                  30

Arg Gly Arg Pro Ser Ser Phe Ile Asp Thr Val Thr Phe Pro Thr Val
        35                  40                  45

Leu Thr Asp Lys Ala Tyr Thr Tyr Arg Val Val Val Ser Gly Lys Asp
    50                  55                  60

Leu Gly Val Arg Pro Ser Tyr Ala Val Glu Ser Asp Gly Ser Gln Lys
65                  70                  75                  80

Ile Asn Phe Leu Glu Tyr Asn Ser Gly Tyr Gly Ile Ala Asp Thr Asn
                85                  90                  95

```
Thr Ile Gln Val Tyr Val Ile Asp Pro Asp Thr Gly Asn Asn Phe Ile
            100                 105                 110

Val Ala Gln Trp Asn Tyr Leu Glu Gln Lys Leu Ile Ser Glu Glu Asp
        115                 120                 125

Leu Asn Ser Ala Val Asp His His His His His His
    130             135                 140
```

USE OF IMMUNOMODULATORY PROTEIN FROM GANODERMA IN INHIBITING CANCER STEM CELLS

FIELD OF THE INVENTION

The present invention relates to a new use of an immunomodulatory protein derived from *Ganoderma* or a recombinant or a composition thereof in inhibiting cancel stem cells. Particularly, the immunomodulatory protein is derived form *Ganoderma microsporum* and the cancel stem cell is oral cancer stem cell.

BACKGROUND OF THE INVENTION

Stem cells have been defined as multipotent, self-renewing cells with the potential to differentiate into multiple cell types. Cancer stem cells (CSCs) are cancer cells (found within tumors or hematological cancers) that possess characteristics associated with normal stem cells, specifically the ability to give rise to all cell types found in a particular cancer sample. CSCs are therefore tumorigenic (tumor-forming), perhaps in contrast to other non-tumorigenic cancer cells. John Dick and his coworkers identify the first cancer stem cell, the leukaemia stem cell (Nature Med. 1997 3, 730-737). The first stem cell identified from a solid tumor is the breast cancer stem cell (Proc. Natl. Acad. Sci. USA 2003 100, 3983-3988). CSCs may generate tumors through the stem cell processes of self-renewal and differentiation into multiple cell types. Such cells are proposed to persist in tumors as a distinct population and cause relapse and metastasis by giving rise to new tumors. Therefore, development of specific therapies targeted at CSCs holds hope for improvement of survival and quality of life of cancer patients, especially for patients with metastatic disease.

The CSCs contain an increased number of multi-drug resistant transporter proteins which pump out chemotherapeutic drugs from the cells. Also, the CSCs were shown to be more resistance to radiation. CSCs comprise a unique subpopulation (often 0.1-10% or so) of a tumor that, relative to the remaining 90% or so of the tumor (i.e., the tumor bulk), are more tumorigenic, relatively more slow-growing or quiescent, and often relatively more chemoresistant than the tumor bulk. Given that conventional therapies and regimens have, in large part, been designed to attack rapidly proliferating cells (i.e. those cancer cells that comprise the tumor bulk), cancer stem cells which are often slow-growing may be relatively more resistant than faster growing tumor bulk to conventional therapies and regimens. A population of CSCs, which gave rise to it, could remain untouched and cause a relapse of the disease.

U.S. Pat. No. 8,846,633 provides a method for inhibiting cancer stem cell like properties and chemoradioresistant properties of cancer or tumor cells comprising delivering miR145 to the cancer or tumor cells, particularly brain tumor and head and neck cancer cells. US 20140045841 provides a method for inhibiting the growth of cancer stem cells, particularly colorectal cancer stem cells, liver cancer stem cells, lung cancer stem cells or breast cancer stem cells, comprising administering to a subject in need thereof a therapeutically effective amount of a compound of antimycin A or a pharmaceutically acceptable salt thereof, together with a pharmaceutically acceptable carrier. Cancer stem cells by virtue of their chemoresistance may contribute to treatment failure, and may also persist in a patient after clinical remission and these remaining cancer stem cells may therefore contribute to relapse at a later date. Accordingly, new therapeutic agents and/or regimens designed to target cancer stem cells are needed.

DETAILED DESCRIPTION OF THE INVENTION

The invention surprisingly found that an immunomodulatory protein from *Ganoderma* can inhibit or kill cancer stem cells, suggesting that the immunomodulatory protein from *Ganoderma* can treat and/or prevent a relapsed, recurred or a refractory cancer.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

In this application, the use of the singular includes the plural, the article "a" or "an" means "at least one", and the use of "or" means "and/or", unless specifically stated otherwise.

In this application, the word "comprise," or variations such as "comprises" or "comprising," indicate the inclusion of any recited integer or group of integers but not the exclusion of any other integer or group of integers in the specified method, structure, or composition.

As used herein, "cancer stem cell" refers to a minor subset of tumor cells that has the ability to self-renewal and generates all cell types present within the tumors. CSCs (also referred as "cancer initiating cell") initiate and sustain tumorigenesis. Cancer stem cells are also typically slow-growing relative to the bulk of a tumor; that is, cancer stem cells are generally quiescent. In certain embodiments, but not all, the cancer stem cell may represent approximately 0.1 to 10% of a tumor.

As used herein, the term "self-renewal" refers to cancer stem cells' ability to give rise to new tumorigenic cancer stem cells to replenish or increase their number.

As used herein, the term "refractory" is most often determined by failure to reach clinical endpoint, e.g., response, extended duration of response, extended disease-free, survival, relapse-free survival, progression-free survival and overall survival. Another way to define being refractory to a therapy is that a patient has failed to achieve a response to a therapy such that the therapy is determined to not be therapeutically effective.

As used herein, "tumor Recurrence" is cancer that has recurred (come back), usually after a period of time during which the cancer could not be detected. The cancer may come back to the same place as the original (primary) tumor or to another place in the body. It is also called recurrent cancer.

As used herein, "inhibit", "prevent" or "reduce," or "inhibiting", "preventing" or "reducing" are used interchangeably herein. These terms refer to the decrease in a measured parameter in a treated cell (tissue or subject) in comparison to an untreated cell (tissue or subject). A comparison can also be made of the same cell or tissue or subject between before and after treatment. The decrease is sufficient to be detectable. In some embodiments, the decrease in the treated cell is at least about 10%, 20%, 30%, 40%, 50%, 60%, 70%, 80%, 90%, or completely inhibited in comparison to an untreated cell.

As used herein, "treatment" or "treating" or "ameliorating" are used interchangeably herein. These terms refer to an approach for obtaining beneficial or desired results including, but not limited to, therapeutic benefit and/or a prophylactic benefit. Therapeutic benefit pertains to eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, "therapeutically effective amount" means an amount sufficient to treat a subject afflicted with a disease or to alleviate a symptom or a complication associated with the disease.

As Used Herein, "Subject" Refers to Either a Human or Non-Human Animal.

The invention provides a method of inhibiting or killing a CSC, comprising administering an effective amount of an immunomodulatory protein derived from *Ganoderma*, or a recombinant or a composition thereof to a subject thereby inhibiting or killing a CSC. The immunomodulatory protein from *Ganoderma*, or a recombinant thereof of the present disclosure can be used to inhibit cancer stem cells. Particularly, the immunomodulatory protein from *Ganoderma*, or a recombinant thereof can inhibit head and neck cancer, preferably, oral cancer stem cells, more preferably, oral squamous cell carcinoma (OSCC). By contacting the CSCs with the effective amount of the immunomodulatory protein from *Ganoderma*, or a recombinant thereof, the CSC can be inhibited or killed.

In one embodiment, the immunomodulatory protein or a recombinant thereof is derived from *Ganoderma lucidum, Ganoderma lucidum, Ganoderma tsugae, Ganoderma microsporum* or *Ganoderma sinensis*. Preferably, the immunomodulatory protein is LZ-8 derived from *Ganoderma lucidum*, FIP-gts derived from *Ganoderma tsugae*, GMI derived from *Ganoderma microsporum*, or FIP-gja derived from *Ganoderma sinensis* or a recombinant thereof.

In one embodiment, the immunomodulatory protein is derived from *Ganoderma microsporum* (GMI) or a recombinant thereof (reGMI). More preferably, the immunomodulatory protein (GMI or reGMI) has the amino acid sequence: (1) -Leu-Ala-Trp-Asn-Val-Lys-(LAWNVK; SEQ ID NO:1) and (2) -Asp-Leu-Gly-Val-Arg-Pro-Ser-Tyr-Ala-Val-(DLGVRPSYAV; SEQ ID NO:2), the amino acid sequence of: MSDTALIFTLAWNVKQLAFDYTPNWGRGRPSSFIDT-VTFPTVLTDKAYTYRVVVSGKD LGVRPSYAVESDG-SQKINFLEYNSGYGIADTNTIQVYVIDPDTGNN-FIVAQWN (SEQ ID NO:3) or the amino acid sequence of EAEAEFMSDTALIFTLAWNVKQLAFDYTPNWGR-GRPSSFIDTVTFPTVLTDKAYTYRVV VSGKDLGVRP SYAVESDGSQKINFLEYNSGYGIADTNTIQVYVIDP-DTGNNFIVAQWNY LEQKLISEEDLNSAVDHHHHHH (SEQ ID NO:4).

In one embodiment, the amount for inhibiting or killing cancer stem cells ranges from about 15 mg to about 75 mg, about 20 mg to about 70 mg, about 20 mg to about 60 mg, about 20 mg to about 55 mg, about 20 mg to about 50 mg, about 20 mg to about 45 mg, about 20 mg to about 40 mg, about 25 mg to about 75 mg, about 25 mg to about 70 mg, about 25 mg to about 65 mg, about 25 mg to about 60 mg, about 25 mg to about 55 mg, about 25 mg to about 50 mg, about 25 mg to about 45 mg, about 25 mg to about 40 mg, about 30 mg to about 75 mg, about 30 mg to about 70 mg, about 30 mg to about 65 mg, about 30 mg to about 60 mg, about 30 mg to about 55 mg, about 30 mg to about 50 mg, about 30 mg to about 45 mg, about 30 mg to about 40 mg, or about 35 mg to about 75 mg, about 35 mg to about 70 mg, about 35 mg to about 65 mg, about 35 mg to about 60 mg, about 35 mg to about 55 mg, about 35 mg to about 50 mg, about 35 mg to about 45 mg or about 35 mg to about 40 mg, of the immunomodulatory protein per kg body weight. Amount between about 36 mg to about 37 mg of the immunomodulatory protein per kg body weight is more preferred.

In another aspect, the invention provides a method of preventing or treating a relapsed, recurred or a refractory cancer, comprising administering an effective amount of an immunomodulatory protein derived from *Ganoderma*, or a recombinant or a composition thereof to a subject thereby preventing or treating a relapse or recurrence of cancer or a refractory caner. Any type of relapsed, recurred or refractory caner can be prevented or treated by the immunomodulatory protein derived from *Ganoderma*, as disclosed in the invention. Preferably, the relapsed, recurred or refractory caner includes but is not limited to prostate, breast, lung, colon, bladder, liver, pancreatic, head and neck cancer and brain cancer. Preferably, the relapsed, recurred or refractory caner is oral cancer, more preferably, oral squamous cell carcinoma.

In one embodiment, the amount for preventing or treating a relapse of cancer ranges from about 15 mg to about 75 mg, about 20 mg to about 70 mg, about 20 mg to about 60 mg, about 20 mg to about 55 mg, about 20 mg to about 50 mg, about 20 mg to about 45 mg, about 20 mg to about 40 mg, about 25 mg to about 75 mg, about 25 mg to about 70 mg, about 25 mg to about 65 mg, about 25 mg to about 60 mg, about 25 mg to about 55 mg, about 25 mg to about 50 mg, about 25 mg to about 45 mg, about 25 mg to about 40 mg, about 30 mg to about 75 mg, about 30 mg to about 70 mg, about 30 mg to about 65 mg, about 30 mg to about 60 mg, about 30 mg to about 55 mg, about 30 mg to about 50 mg, about 30 mg to about 45 mg, about 30 mg to about 40 mg, or about 35 mg to about 75 mg, about 35 mg to about 70 mg, about 35 mg to about 65 mg, about 35 mg to about 60 mg, about 35 mg to about 55 mg, about 35 mg to about 50 mg, about 35 mg to about 45 mg or about 35 mg to about 40 mg, of the immunomodulatory protein per kg body weight.

Amount between about 36 mg to about 37 mg of the immunomodulatory protein per kg body weight is more preferred.

In one embodiment, the immunomodulatory protein or a recombinant thereof is derived from *Ganoderma lucidum, Ganoderma lucidum, Ganoderma tsugae, Ganoderma microsporum* or *Ganoderma sinensis*. Preferably, the immunomodulatory protein is LZ-8 derived from *Ganoderma lucidum*, FIP-gts derived from *Ganoderma tsugae*, GMI derived from *Ganoderma microsporum*, or FIP-gja derived from *Ganoderma sinensis* or a recombinant thereof.

In one embodiment, the immunomodulatory protein is derived from *Ganoderma microsporum* (GMI) or a recombinant thereof (reGMI). More preferably, the immunomodulatory protein (GMI or reGMI) has the amino acid sequence: (1) -Leu-Ala-Trp-Asn-Val-Lys-(LAWNVK; SEQ ID NO:1) and (2) -Asp-Leu-Gly-Val-Arg-Pro-Ser-Tyr-Ala-Val-(DL-GVRPSYAV; SEQ ID NO:2), the amino acid sequence of: MSDTALIFTLAWNVKQLAFDYTPNWGRGRPSSFIDT-VTFPTVLTDKAYTYRVVVSGKD LGVRPSYAVESDG-SQKINFLEYNSGYGIADTNTIQVYVIDPDTGNN-FIVAQWN (SEQ ID NO:3), or the amino acid sequence of EAEAEFMSDTALIFTLAWNVKQLAFDYTPNWGR-GRPSSFIDTVTFPTVLTDKAYTYRVV VSGKDL-GVRPSYAVESDGSQKINFLEYNSGY-GIADTNTIQVYVIDPDTGNNFIVAQWNY LEQKLISEEDLNSAVDHHHHHH (SEQ ID NO:4).

The immunomodulatory protein or a recombination thereof of the invention can be administered to a patient either alone or in pharmaceutical compositions where it is mixed with suitable carriers and excipients. The immunomodulatory protein or a recombination thereof or a composition of the invention can be administered parenterally, such as by intravenous injection or infusion, intraperitoneal injection, subcutaneous injection, or intramuscular injection. The immunomodulatory protein or a recombination thereof or a composition can be administered orally or rectally through appropriate formulation with carriers and excipients to form tablets, pills, capsules, liquids, gels, syrups, slurries, suspensions and the like. The immunomodulatory protein or a recombination thereof or a composition can be administered topically, such as by skin patch. The immunomodulatory protein or a recombination thereof or a composition can be formulated into topical creams, skin or mucosal patch, liquids or gels suitable to topical application to skin or mucosal membrane surfaces. The immunomodulatory protein or a recombination thereof or a composition can be administered by inhaler to the respiratory tract for local or systemic treatment of cancers.

The dosage of the immunomodulatory protein or a recombination thereof or a composition suitable for use according to the present invention can be determined by those skilled in the art on the basis of the disclosure herein. The medicament will contain an effective dosage (depending upon the route of administration and pharmacokinetics of the active agent) of Suitable pharmaceutical carriers and excipients are suitable for the particular route of administration of the formulation (i.e., oral, parenteral, topical or by inhalation). immunomodulatory protein or a recombination thereof is mixed into the pharmaceutical composition by means of mixing, dissolving, granulating, dragee-making, emulsifying, encapsulating, entrapping or lyophilizing processes. The pharmaceutical compositions for parenteral administration include aqueous solutions of the inventive polypeptide in water-soluble form. Additionally, suspensions of the inventive polypeptide may be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. The suspension may optionally contain stabilizers or agents to increase the solubility of the complex or combination to allow for more concentrated solutions.

In another embodiment, the immunomodulatory protein or a recombination thereof can be combined with an anti-CSC agent for combination therapy in inhibiting or killing CSCs or treating and/or preventing a relapsed, recurred or refractory cancer. The immunomodulatory protein a recombinant thereof also can be combined with an anti-CSC agent as a pharmaceutical composition. That is, the invention provides a pharmaceutical composition comprising the immunomodulatory protein or a recombinant thereof and an additional anti-CSC agent.

Without further elaboration, it is believed that one skilled in the art can utilize the present invention to its fullest extent on the basis of the preceding description. The following examples are, therefore, to be construed as merely illustrative and not a limitation of the scope of the present invention in any way.

EXAMPLE

The recombinant immunomodulatory protein derived from *Ganoderma microsporum* (hereafter referred to as "recomGMI") was manufactured by Mycomagic Biotechnology Co., Ltd., according to the method described in U.S. Pat. No. 7,601,808 and has an amino acid sequence shown in FIG. 3B of U.S. Pat. No. 7,601,808. The recomGMI was used in the following assays.

Example 1

Cell Proliferation/Survival Determination by MTT Assay

SG and CSCs were plated in wells of 96-well-plate as $1 \times 10^4$ cells/well in 0.1% DMSO or different concentration of recomGMI-containing medium and cultured at 37° C. for 24 hr. Cell proliferation/survival was determined by MTT (3-(4,5-dimethylthiazol-2-yl)-2,5-diphenyl tetrazolium bromide) assay. The 570 nm absorbance of DMSO treated group was set as 100% and data were presented as percentage of DMSO control.

Figure 1:
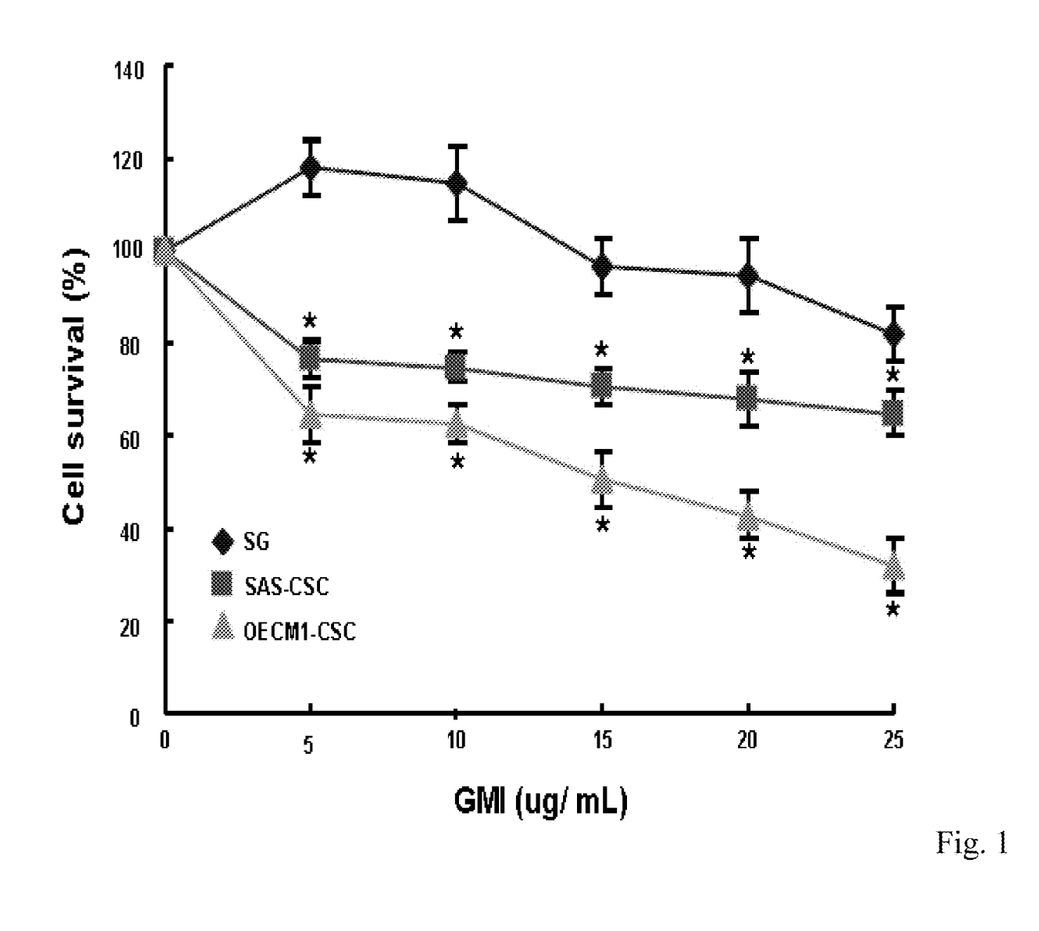
FIG. 1 shows the cell viability effect of GMI in normal epithelial cells and oral CSCs.

As shown in FIG. 1, the above MTT assay proved that recomGMI (0, 5, 10, 15, 20 and 25 μg/mL) can significantly inhibit proliferation rate of 28% and 64% in SAS-CSC and OECM1-CSC within 24 hours in a dose-dependent manner, while recomGMI is non-toxic to the normal oral epithelial cells (SG).

Example 2

ALDEFLUOR Assay

An ALDEFLUOR assay kit was purchased from StemCell Technologies, Inc. (Vancouver, BC, Canada). For this assay, $1 \times 10^5$ cells were suspended in 50 μl of assay buffer, and ALDEFLUOR was added to the cell suspensions for a final concentration of 1 μM. For ALDH1 inhibitor control, DEAB was added to a final concentration of 150 μM. Cells were then incubated at 37° C. for 45 min and were stained with 7-AAD on ice for 5 min. After washing the cells with PBS, live cells (7AAD-) positive for green fluorescence were analyzed by flow cytometry (FACSCalibur™, BD Biosciences) to compare the fluorescence intensity of the DEAB-treated samples. High fluorescence was associated with high ALDH activity (ALDH+ cells).

Figure 2:
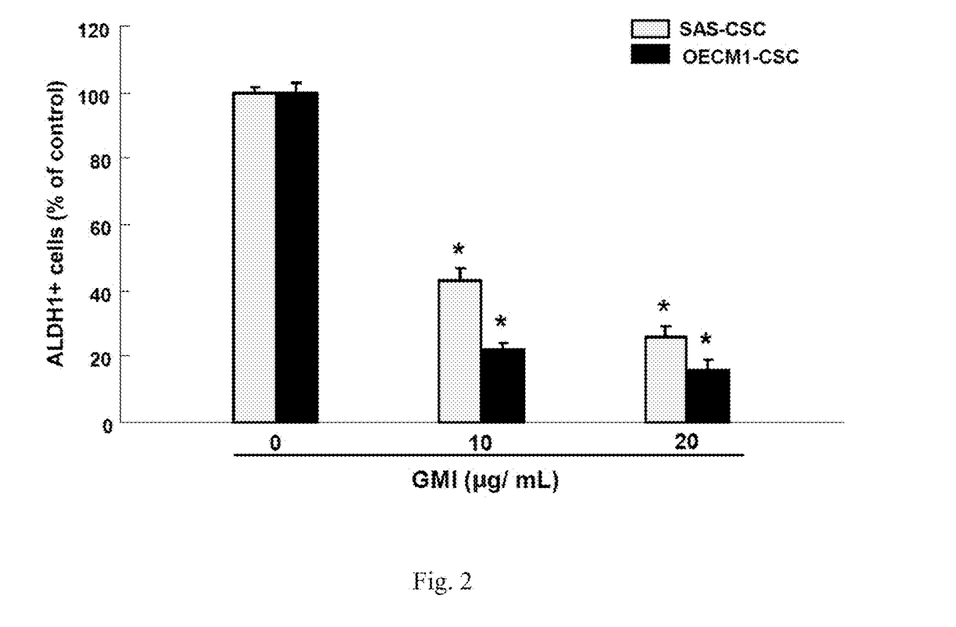
FIG. 2 shows that GMI effectively eliminates ALDH1 activity.

ALDH1+ has been proposed to exhibit CSC properties and have been used as CSC functional markers for oral CSC. As shown in FIG. 2, recomGMI treatment can effectively reduce 55% and 72% ALDH1 activity of both SAS-CSC and OECM1-CSC cells in a concentration-dependent manner.

Example 3

Flow Cytometry Assay

Cells were stained with anti-CD44 antibody conjugated to phycoerythrin (Miltenyi Biotech., Auburn, Calif., USA), with labeling according to the manufacturer's instructions. Red (>650 nm) fluorescence emission from 10,000 cells illuminated with blue (488 nm) excitation light was measured with a FACSCalibur (Becton Dickinson) using Cell-Quest software.

Figure 3:
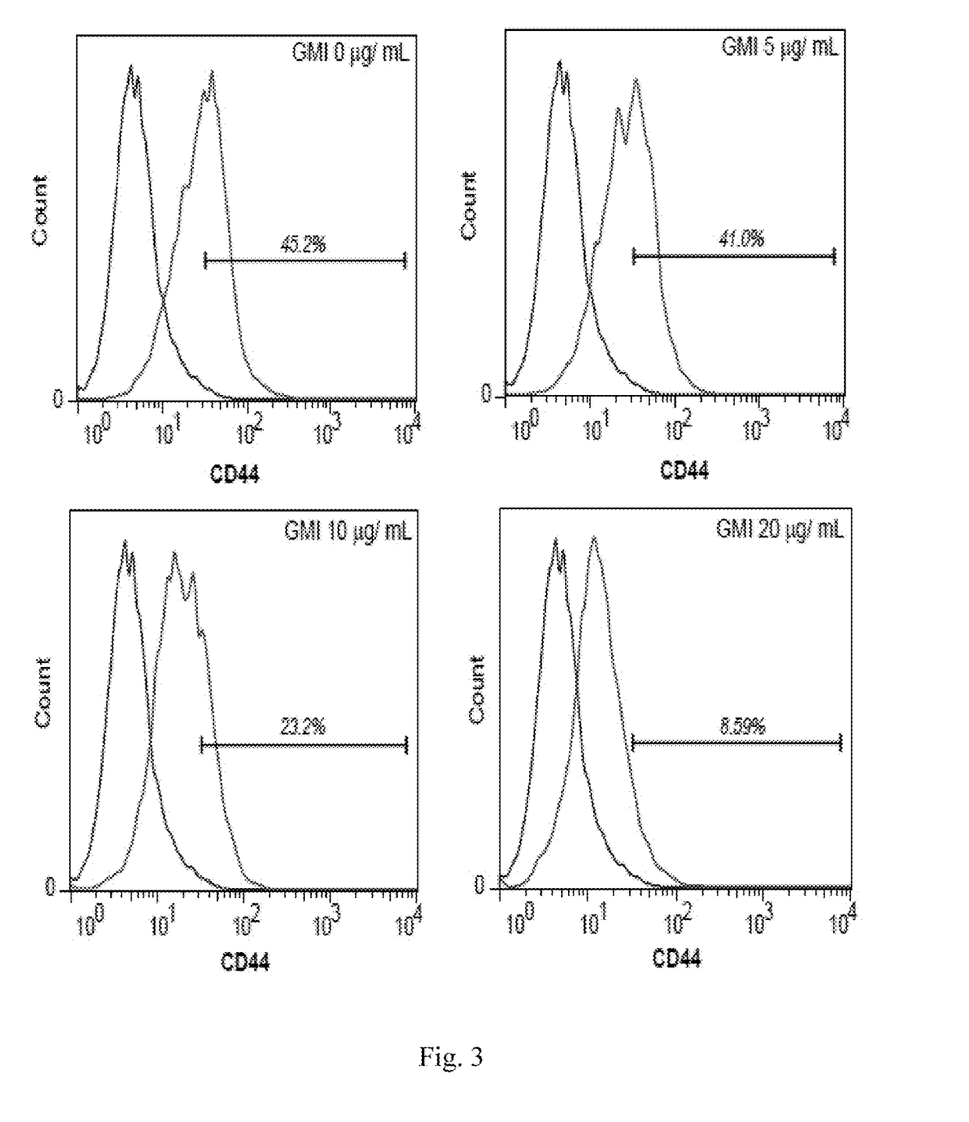
FIG. 3 shows that GMI effectively inhibits CD44 positivity.

CD44 could be also used as potential markers for the isolation of CSC. FIG. 3 shows that recomGMI in different concentrations (0, 5, 10, 15, 20 and 25 µg/mL) can effectively reduce CD44 expression of SAS-CSC cells.

Example 4

Tumor Sphere-Forming Assay

Tumor cells [SAS and OECM1] were dissociated and cultured as primary sphere-forming oral CSC in modified DMEM/F-12 supplemented with N2 (R&D), 10 ng/mL epidermal growth factor (EGF, Invitrogen), 10 ng/mL basic fibroblast growth factor (bFGF, Invitrogen), and penicillin/streptomycin at $10^4$ live cells/low-attachment 10 cm dish (Corning Inc., Corning, N.Y.), and the medium was changed every other day until the tumor sphere formation was observed in about 1 weeks. For serial passage of sphere cells, single cells be obtained from accurtase treated spheroids and the cell density of passage will be 10000 cells/ml in the serum-free medium as described above.

Figure 4:
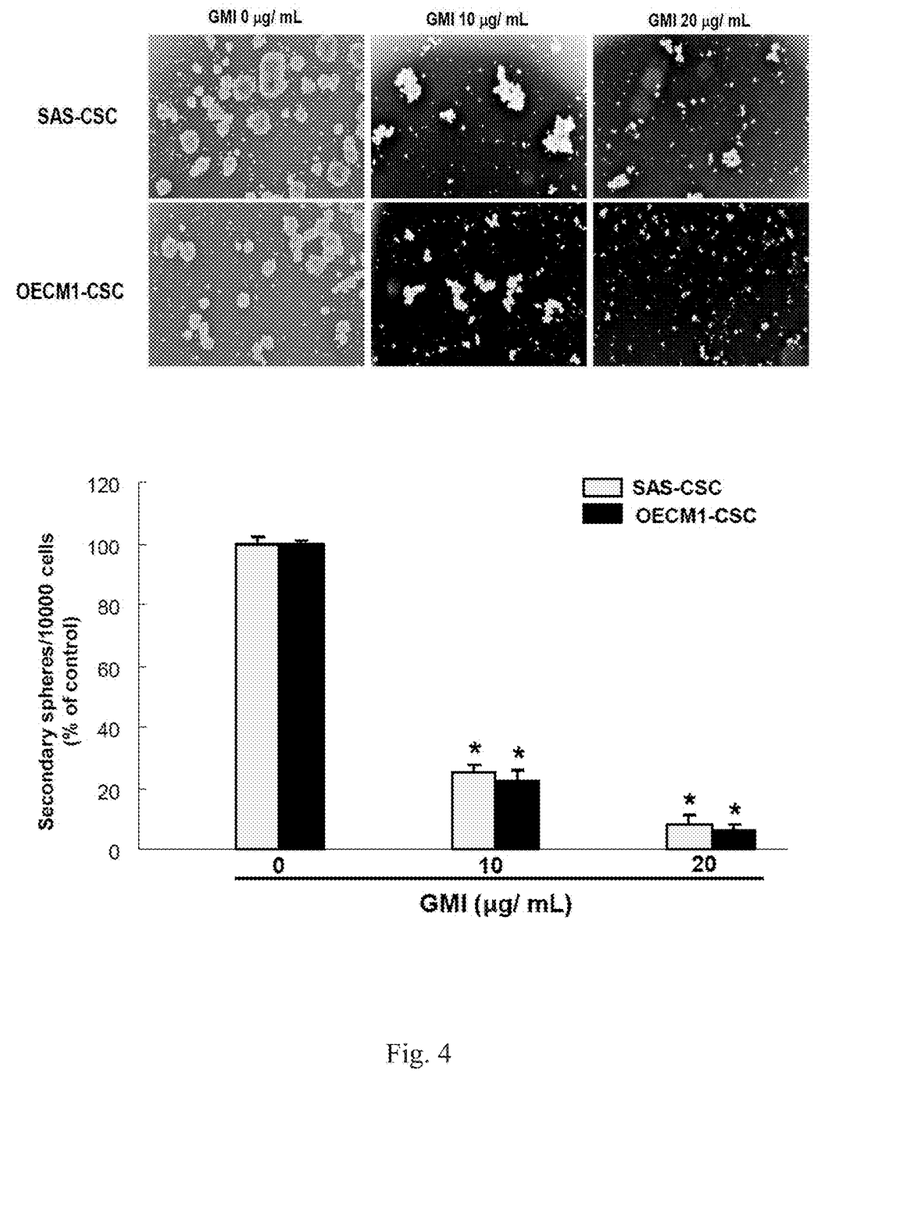
FIG. 4 shows inhibition of self-renewal property in oral CSCs under GMI treatment.

Successful sphere formation phenotypes after serial passages of culture, one of indexes for evaluating the persistent self-renewal property of CSC. To investigate the effect of recomGMI in targeting self-renewal properties of oral CSC, we evaluated the secondary sphere-forming ability with recomGMI treatment in primary tumor sphere-forming oral CSC. FIG. 4 shows that recomGMI can dose-dependently reduce the ability of oral cancer stem cells in forming secondary sphere bodies.

Example 5

In Vitro Cell Invasion Analysis

The 24-well plate Transwell® system with a polycarbonate filter membrane of 8-µm pore size (Corning, United Kingdom) was employed to evaluate the invasion ability of cells. The membrane was coated with Matrigel™ (BD Pharmingen, NJ, USA). The cancer cell suspensions were seeded to the upper compartment of the Transwell chamber at the cell density of $1\times10^5$ in 100 ml within serum-free medium. The lower chamber was filled with media with 10% serum After 24 hours of incubation, the medium was removed and the filter membrane was fixed with 4% formalin for 1 hour. Subsequently, the remaining cells of the filter membrane faced the lower chamber was stained with Crystal Violet. The invasion cancer cells were then visualized and counted from 5 different visual areas of 100-fold magnification under an inverted microscope.

Figure 5:
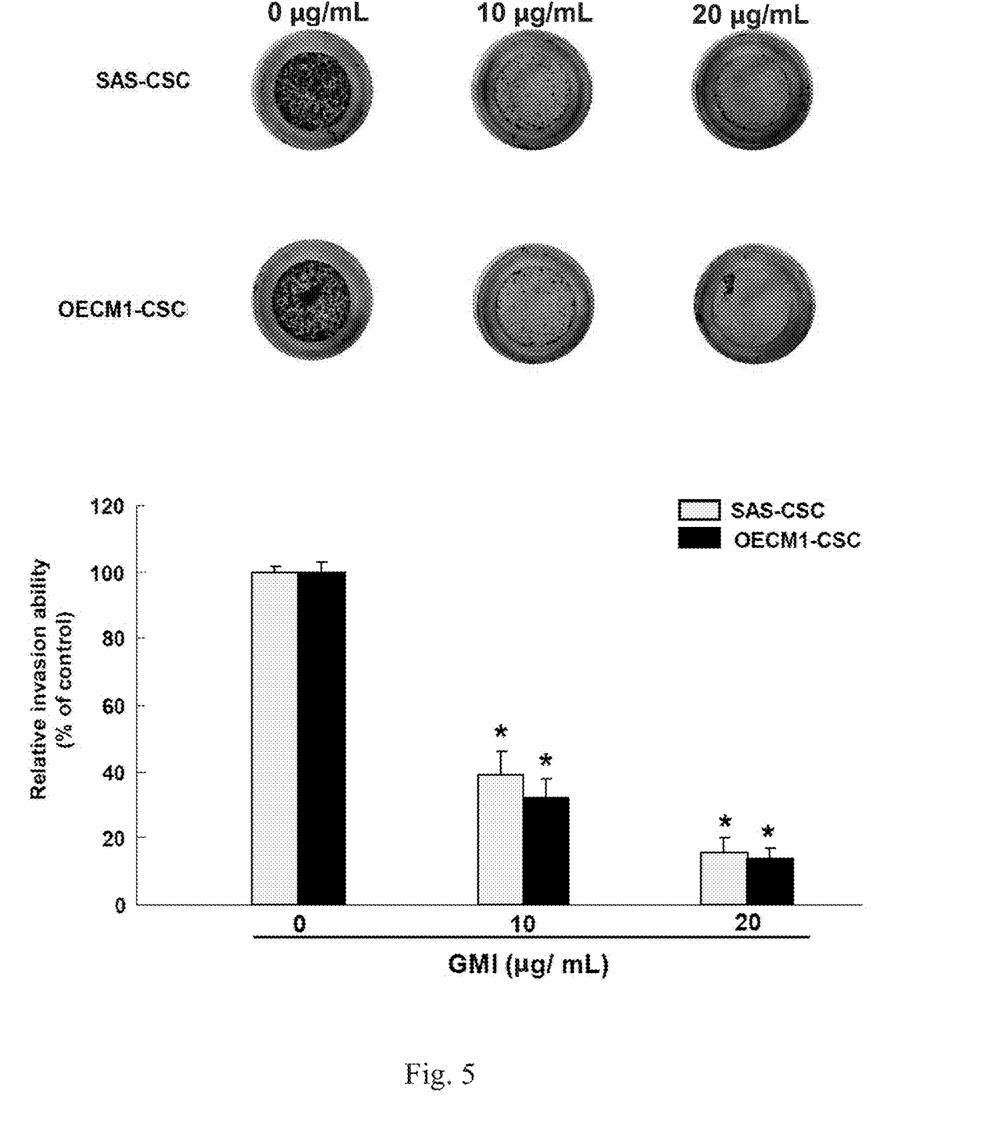
FIG. 5 shows that GMI abrogates invasion capacity of oral CSCs.

Since CSC appear to play a significant role in metastasis. Single cell suspension of control- or recomGMI-treated oral CSC were used for analysis of their metastatic capacity in vitro FIG. 5 shows that recomGMI (0, 10, and 20 µg/mL) can inhibit invasion ability of 82% and 84% in SAS-CSC and OECM1-CSC.

Example 6

Soft Agar Colony Forming Assay

Figure 6:
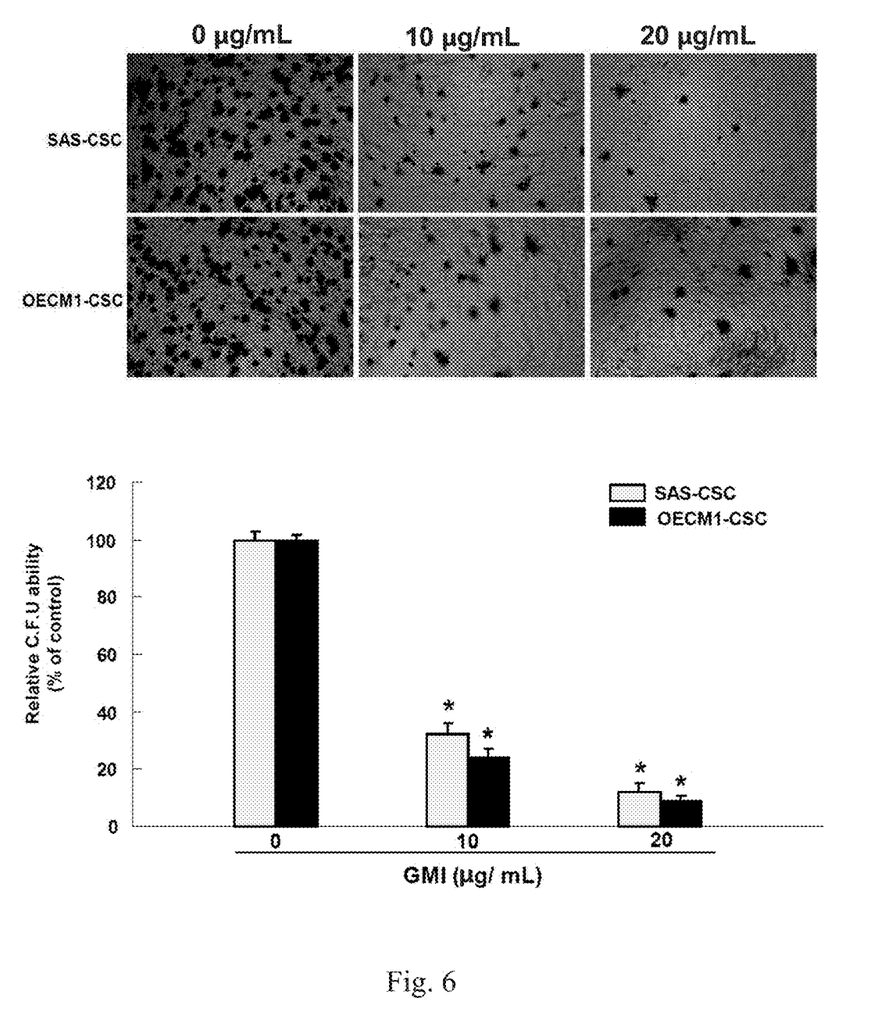
FIG. 6 shows that GMI effectively attenuates clonogenicity.

Six-well culture dish was coated with 2 ml bottom agar (Sigma-Aldrich) mixture (DMEM, 10% (v/v) FCS, 0.6% (w/v) agar). After the bottom layer was solidified, 2 ml top agar-medium mixture (DMEM, 10% (v/v) FCS, 0.3% (w/v) agar) containing $2\times10^4$ cells was added, and the dishes were incubated at 37° C. for 4 weeks. Plates were stained with 0.005% Crystal Violet then the colonies were counted. The number of total colonies with a diameter ≥100 was counted over five fields per well for a total of 15 fields in triplicate experiments. FIG. 6 shows that recomGMI can dose-dependently inhibit colony forming ability of 89% and 92% in SAS-CSC and OECM1-CSC.

Example 7

In Vivo Imaging Measurement of Tumor Growth in Nude Mice

All procedures involving animals were in accordance with the institutional animal welfare guidelines of the Chung Shan Medical University. For the nude mice xenograft model, 5-6 weeks old immuno-deficient nude mice (BALB/c nu/nu mice) weighing 18-22 g were used. The mice were housed with a regular 12 h light/12 h dark cycle and ad libitum access to standard rodent chow diet (Laboratory Rodent Diet 5001, LabDiet, St. Louis, Mo.) and were kept in a pathogen-free environment at the Laboratory Animal Unit. SAS-CSC ($1\times10^4$ cells/0.1 mL/mouse) were injected subcutaneously into the right front axilla. Eight days post-implantation, the mice were randomly divided into three groups (N=3 for each group) and fed by oral gavage with saline (control) and GMI (150 µg/day/kg). BLI was performed using an IVIS50 animal imaging system (Xenogen Corp.). The volume was calculated (according to the following formula: [length×width]/2), and then analyzed using Image-Pro Plus software. Body weight was assessed daily after cell injection. After 20 days, the animals were euthanized, and the primary tumors were isolated and weighed.

Figure 7:
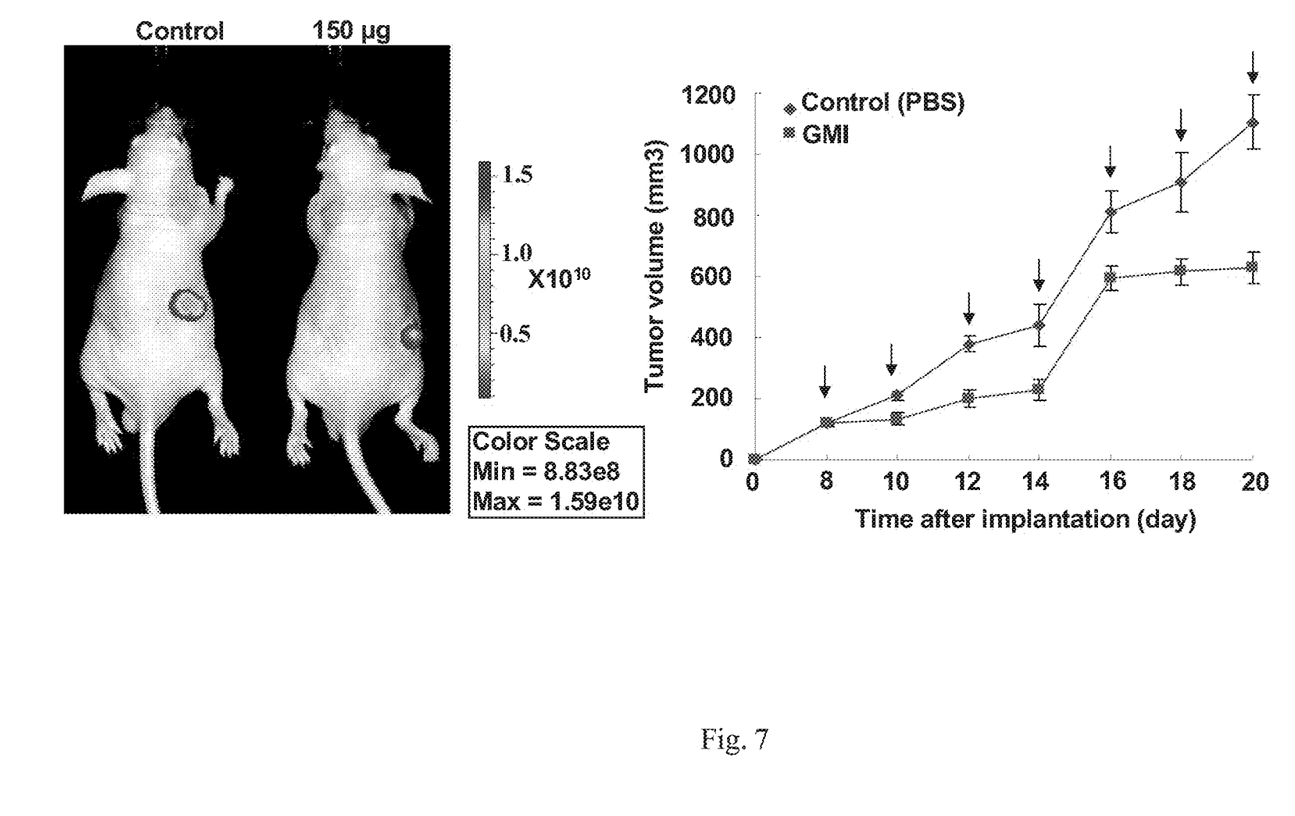
FIG. 7 shows that therapeutic delivery of GMI oral CSCs-transplanted mice attenuates tumor progression in vivo.

To verify the in anti-tumor effects of recomGMI against oral CSC in vivo, oral CSC-bearing nude mice were treated with saline or recomGMI by oral gavage. FIG. 7 shows that tumor formation in all recipients was reduced following xenotransplantation of oral CSC that received oral gavage recomGMI treatment on day 20 as compared to control animals. Moreover, by day 20, recomGMI feeding (150 µg/day/kg) induced a reduction in tumor volume of oral CSC-transplanted nude mice.

What is claimed is:

1. A method of treating a relapsed, recurred or a refractory oral cancer or oral squamous cell carcinoma (OSCC) in a subject in need thereof, comprising administering an effective amount of an immunomodulatory protein derived from *Ganoderma*, or a recombinant or a composition thereof to the subject thereby treating a relapse or recurrence of oral cancer or OSCC or a refractory oral cancer or OSCC, wherein the immunomodulatory protein has the amino acid sequence as shown in SEQ ID NO: 3.

2. The method of claim 1, the amount for treating a relapsed, recurred or a refractory oral cancer or oral squamous cell carcinoma (OSCC) in a subject in need thereof ranges between about 15 mg to about 75 mg weight of the immunomodulatory protein per kg body weight.

* * * * *